US008230733B2

(12) United States Patent
Pierce et al.

(10) Patent No.: US 8,230,733 B2
(45) Date of Patent: Jul. 31, 2012

(54) SPRING MEMBER TEST APPARATUS

(75) Inventors: Bruce Frederick Pierce, Farmington Hills, MI (US); Alexander Gregory Livshiz, Farmington Hills, MI (US); Liang Tang, Ann Arbor, MI (US); Ian D. S. MacLachlan, Redford, MI (US); Andre Luis Beduschi, Lauro de Fretas (BR); Edwin R. Dubin, Belleville, MI (US); David J Dudonis, Romulus, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 541 days.

(21) Appl. No.: 12/465,902

(22) Filed: May 14, 2009

(65) Prior Publication Data

US 2010/0288041 A1 Nov. 18, 2010

(51) Int. Cl.
*G01L 1/04* (2006.01)
(52) U.S. Cl. .......................................................... 73/161
(58) Field of Classification Search ........................ None
See application file for complete search history.

(56) References Cited

U.S. PATENT DOCUMENTS

| | | | | |
|---|---|---|---|---|
| 3,610,031 A | * | 10/1971 | Clark et al. ...................... | 73/795 |
| 4,607,531 A | * | 8/1986 | Meline et al. .................... | 73/794 |
| 4,658,656 A | * | 4/1987 | Haeg ................................ | 73/669 |
| 4,951,504 A | | 8/1990 | Klock et al. .................. | 73/117.1 |
| 5,088,333 A | | 2/1992 | Kiely et al. ................. | 73/862.53 |
| 6,199,427 B1 | | 3/2001 | Kroll et al. ....................... | 73/161 |

FOREIGN PATENT DOCUMENTS

UA 28 592 U 9/2007

OTHER PUBLICATIONS

Science Direct—Analysis and Optimiztion of a Composite Leaf Spring—Mahmood M. Shokrieh and Davood Rezaaei—Feb. 19, 2003.
Multi-Leaf Spring and Hotchkiss Suspension—CAE Simulation—Peiyong Qin et al.—2002.
R4 Tech—Rear Suspension Development Initiative—Sanluis Rassini—Oct. 2008.
Leaf Spring Modeling—Niklas Philipson—Sep. 4-5, 2006—The Modelica Association.

* cited by examiner

*Primary Examiner* — Harshad R Patel
(74) *Attorney, Agent, or Firm* — L.C. Begin & Associates, PLLC

(57) ABSTRACT

An apparatus is provided for loading a spring member secured on the apparatus. The apparatus includes a first mechanism for applying a translational loading to the spring member, and a second mechanism for applying a torsional loading to the spring member. The first mechanism includes a plurality of first elements, and the second mechanism includes a plurality of second elements. Each first element of the plurality of first elements is physically spaced apart from each second element of the plurality of second elements to aid in preventing interference between the first and second mechanisms during operation of the first and second mechanisms.

20 Claims, 3 Drawing Sheets

SPRING MEMBER TEST APPARATUS

BACKGROUND OF THE INVENTION

The present invention relates generally to apparatuses for testing energy absorption and return devices and, more particularly, to embodiments of an apparatus for testing a design of a spring member to be incorporated into a vehicle suspension system.

Analytical methods and systems are known for designing and testing spring members incorporated into suspension systems in vehicles. During operation of a vehicle, leaf springs coupled to an axle in a vehicle suspension system are subjected to both torsional loading due to axle wind-up and vertical loading due to the weight of the vehicle. Both of these modes may contribute to operational failure of the spring. However, many analytical methods and testing systems account for only the vertical load component of the total force acting on the spring member.

SUMMARY OF THE INVENTION

In one aspect f the present invention, an apparatus is provided for loading a spring member secured on the apparatus. The apparatus includes a first mechanism for applying a translational loading to the spring member, and a second mechanism for applying a torsional loading to the spring member. The first mechanism includes a plurality of first elements, and the second mechanism includes a plurality of second elements. Each first element of the plurality of first elements is physically spaced apart from each second element of the plurality of second elements to aid in preventing interference between the first and second mechanisms during operation of the first and second mechanisms.

DETAILED DESCRIPTION

FIGS. 1-6 show one embodiment of an apparatus 10 for testing a design of a spring member to be incorporated into a vehicle suspension system. The embodiments of the test apparatus shown herein simulate attachment of a leaf spring 12 to a vehicle as seen in a Hotchkiss-type suspension. The embodiments of the test apparatus also enable simulation of the loading on a leaf spring during various operational modes of the vehicle. However, the principles and embodiments of the mechanism described herein may also be adapted for simulating the loading on other types of spring members under any of a variety of loading conditions.

Figure 1:
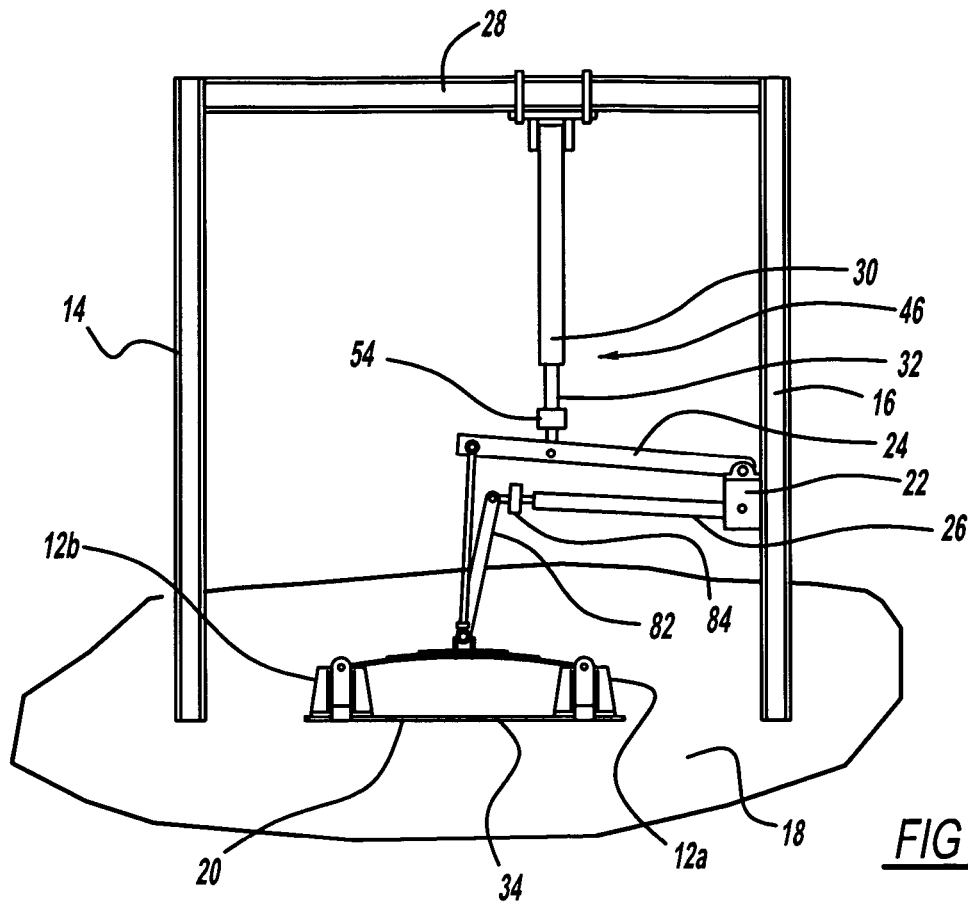
FIG. 1 is a side view of a testing apparatus in accordance with an embodiment of the present invention.
Figure 3:
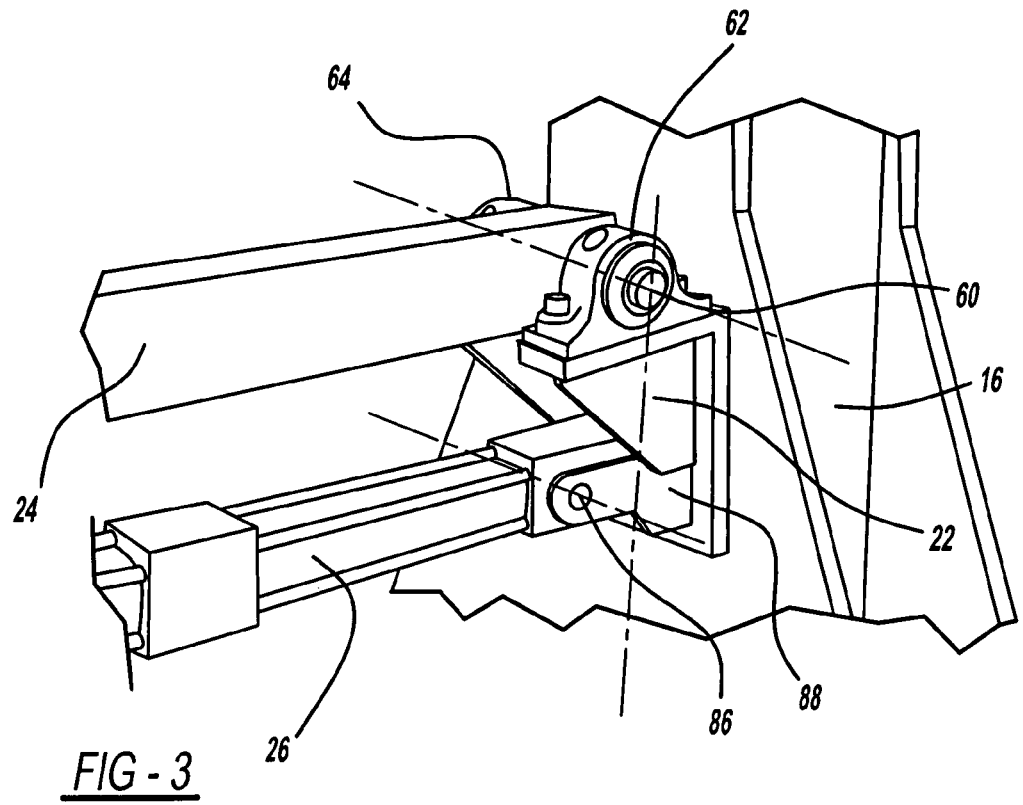
FIG. 3 is a perspective view showing attachment of vertical force arm and a hydraulic cylinder to a support column in accordance with an embodiment of the present invention.

Referring to FIG. 1, a frame structure for supporting elements of the test apparatus includes a pair of steel support columns 14 and 16 are bolted or otherwise secured to the floor of a test area (generally designated 18). Support columns 14 and 16 are spaced apart a sufficient distance to permit a spring mounting base 20 (described below) for spring member 12 to be secured to the test area floor between the columns. Referring to FIGS. 1 and 3, a mounting bracket 22 is secured to support column 16 to enable rotatable attachment of both a vertical force input arm 24 (described below) and a hydraulic cylinder 26 to column 16. Bracket 22 may be welded to column 16, or the bracket and column may be configured to permit the bracket to be repositioned and attached to the column at a variety of locations along a predetermined portion of the column length. This feature facilitates reconfiguration of the test apparatus to accommodate different test requirements and/or the testing of a variety of different spring designs on a variety of different simulated vehicle configurations or spring mounting arrangements.

The frame structure for supporting elements of the test apparatus also includes a bridge 28 spanning the distance between support columns 14 and 16 and is connected to each of the support columns. Bridge 28 overlies spring mounting base 20 so that a hydraulic cylinder 30 suspended from the bridge is positioned to engage vertical force input arm 24 (described below) to apply a force to the arm. Cylinder 30 is suspended from bridge 28 such that an axis along which a piston shaft 32 of the cylinder travels is substantially vertical.

Figure 4:
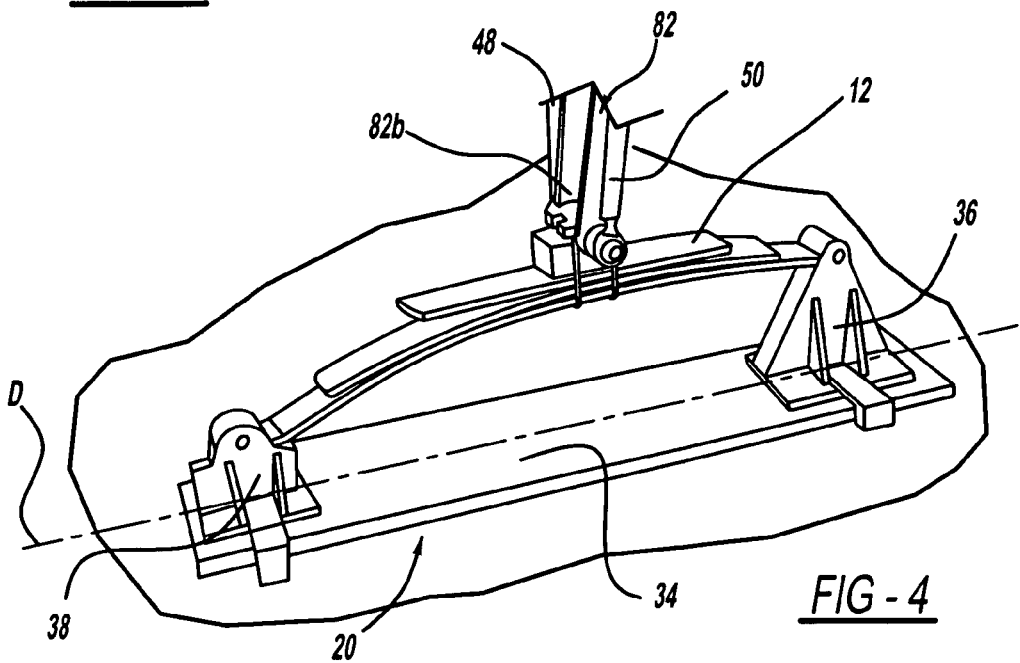
FIG. 4 is a perspective view showing attachment of a spring member to a spring mounting base in accordance with an embodiment of the present invention.

Referring to FIGS. 1 and 4, spring mounting base 20 is positioned and secured between support columns 14 and 16 and directly below bridge 28. Spring mounting base 20 includes a base portion 34, a first mounting block 36 securable to the base portion, and a second mounting block 38 securable to the base portion opposite, and in alignment with, first mounting block 36. Base portion 34 may be secured to the test area floor, and/or the base portion may be secured to one or more of support columns 14 and 16. The base portion 34 may also be secured to the floor area 18 or to support columns 14 and/or 16 so as to permit repositioning and securement of the mounting base 20 along an axis connecting the support columns 14 and 16. This enables the portion of the spring along which the testing forces are applied to be adjusted to a certain degree. These flexible positioning and securement features facilitate reconfiguration of the test apparatus to accommodate different test requirements and/or the testing of a variety of different spring designs on a variety of different simulated vehicle configurations or spring mounting arrangements.

First and second mounting blocks 36 and 38 are configured to enable attachment of end portions of leaf spring 12 thereto, in a manner that duplicates or simulates attachment of the leaf spring ends to a vehicle. In the embodiment shown in FIGS. 1-5, a first end 12a of the leaf spring 12 may be rotatably attached to first mounting block 36 using a bushing or other bearing structure (not shown) secured within a first eye of the spring and a shaft or pin (not shown) press-fit into the bushing and secured to the first mounting block. This arrangement permits the end of the spring to rotate with respect to first mounting block 36. A second end 12b of the spring is attached to second mounting block 38 by rotatably securing a portion of a shackle (not shown) to a second eye formed at a second end of the spring. Another portion of the shackle is then rotatably connected to second mounting block 38 to couple the second end of the spring to the second mounting block.

These attachments duplicate or simulate attachment of the spring to a vehicle. Other methods for attaching the spring ends to the mounting blocks are also contemplated, depending on the particular spring geometry, spring attachment modes, and other requirements of a particular testing application.

To facilitate testing of springs having different lengths, first mounting block 36 and/or second mounting block 38 may be attached to base portion 34 such that one or more of the mounting blocks are repositionable and securable in multiple positions along an axis "D" connecting the mounting blocks.

In a particular embodiment (not shown), one or more of first and second mounting blocks 36 and 38 are slidably positioned in a rail extending along axis "D", to facilitate ease of relocation of the mounting block(s) while ensuring that axial alignment of the mounting blocks is maintained. Means (for example, clamping members) are then provided to secure the movable mounting block(s) in the desired position along the rail.

In an alternative embodiment (not shown), a series of threaded holes are formed in base portion 34 along axis "D" for receiving therein complementary bolts (not shown) inserted through the mounting block(s) to secure the blocks in desired positions corresponding to the hole locations. Other methods are also contemplated for enabling repositioning and securement of one or more of the mounting blocks 36 and 38.

First mounting block 36 and/or second mounting block 38 may also be designed to permit a vertical distance between base portion 34 and the attachment points of either or both of spring end portions 12a and 12b to be varied according to the requirements of a particular application. This feature enables control of the distance between base portion 34 and the portion of the spring to which the testing forces are applied. This, along with suitable control of the stroke length of the piston shaft 32 of cylinder 30 enables control of the total deflection or length of vertical travel of the portion of the spring to which the testing forces are applied. This feature also generally facilitates reconfiguration of the test apparatus to accommodate different test requirements and/or the testing of a variety of different spring designs on a variety of different simulated vehicle configurations or spring mounting arrangements.

The spring mounting base elements should enable positioning and securement of the end portions of spring 12 so that attachment points of the spring can be specified with respect to reference plane(s) or a coordinate system defined by a user in terms of the support column(s), floor area, or other static elements.

Referring again to FIGS. 1 and 2, testing apparatus 10 includes a vertical force actuator mechanism (generally designated 46) configured to apply a translational testing load to the spring member 12 along a substantially vertical plane. Actuator mechanism 46 includes an actuator (in the embodiment shown, a hydraulic cylinder 30) for applying a force to other elements of the mechanism, vertical force arm 24 connected to the cylinder 30 and rotatably coupled to support column 16, and at least one link rotatably coupled to force arm 24 and to an axle tube fixture 52 (described below) for transmitting an actuation force from the cylinder to the axle tube fixture. In the embodiment shown in FIGS. 1-6, a pair of links 48, 50 are rotatably coupled to force arm 24 and to axle tube fixture 52. Vertical force actuator mechanism 46 applies a force to the axle tube fixture to urge movement of the fixture along a plane, in a manner described in greater detail below.

Cylinder 30 is suspended from bridge 28 so as to enable positionability and securement of the actuator mechanism at any point along substantially the entire span of the bridge. A load cell 54 (for example, a strain gauge load cell) may be attached to piston shaft 32 of the cylinder 30 to enable measurement of the force profile applied by the cylinder 30 to the spring 12 in a known manner.

It is understood that all of the test apparatus elements and the connections between these elements are structured to accommodate the loads resulting from application of prescribed test forces to the spring members, while maintaining the structural integrity and rigidity of the elements of the testing apparatus.

In the embodiment shown in FIGS. 1-5, vertical force arm 24 is formed from a pair of parallel arm members separated by a plurality of spacers and secured together (using bolts or welds, for example) to form a single, movable piece. Alternatively, the vertical force arm 24 may be formed from a single member.

Vertical force arm 24 is mounted in the testing apparatus so as to transmit a translational loading produced by actuator mechanism 46 in a vertical plane to spring 12 attached to mounting base 34. Vertical force arm 24 is rotatably connected to bracket 22 via a shaft 60 extending between a pair of pillow block bearings 62, 64 or other suitable bearing mechanisms.

Figure 2:
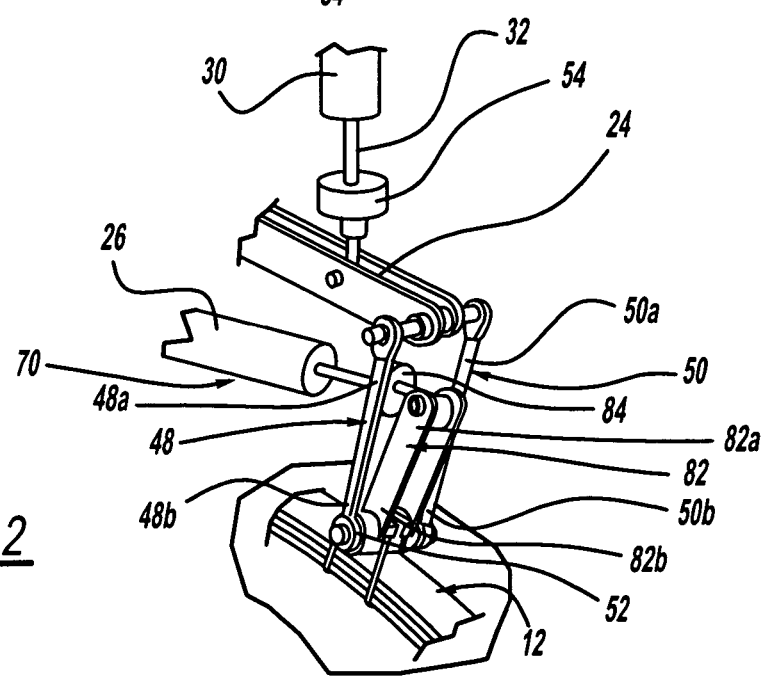
FIG. 2 is a perspective view showing attachment of a vertical force actuator mechanism and a torque actuator mechanism to an axle tube fixture, in accordance with an embodiment of the present invention.
Figure 5:
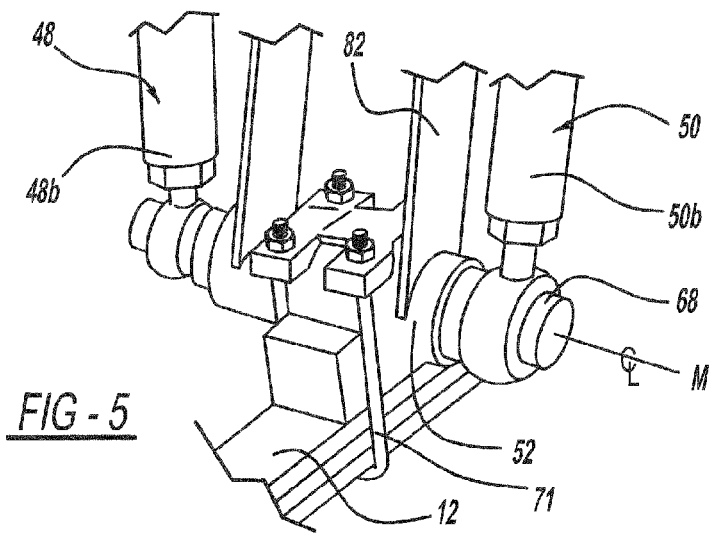
FIG. 5 is a perspective view showing attachment of a vertical force actuator mechanism, a torque actuator mechanism, and a spring member to an axle tube fixture, in accordance with an embodiment of the present invention.

Referring to FIGS. 2 and 5, links 48 and 50 each have respective first ends 48a, 50a and second ends 48b, 50b. Link first ends 48a, 50a are rotatably coupled to vertical force arm 24. Link second ends 48b, 50b may be rotatably mounted in or coupled to a shaft or pin 68 extending through axle tube fixture 52. Forces from vertical force actuator mechanism 46 are transmitted through vertical force arm 24 to links 48 and 50, and through the links to pin 68. Motion of the pin 68 results in a corresponding motion of axle tube fixture 52 coupled to the pin, resulting in motion of the portion of the spring 12 attached to the axle tube fixture.

In a particular embodiment, links 48 and 50 are detachably coupled to shaft 68 so that the vertical force actuator mechanism 46 can be decoupled from the axle tube fixture 52. This enables a torsional load to be applied to the axle tube fixture as described below, without the simultaneous application of a vertical load.

In the embodiment shown herein, axle tube fixture 52 is generally cylindrical and has a central opening extending therethrough for receiving shaft 68 therein. A bushing or bearing structure (not shown) is provided between fixture 52 and shaft 68 to enable the shaft to rotate freely within the opening.

Axle tube fixture 52 simulates a vehicle axle to which a portion of a leaf spring 12 is attached. The spring 12 is attached to the axle tube fixture using "U"-bolts 71 identical to, or substantially similar to, the "U"-bolts used for attachment of the spring design to an actual vehicle axle.

While the general configuration of the axle tube fixture 52 shown in FIG. 5 is suitable for testing a variety of leaf spring designs, the particular dimensions of the axle tube fixture used for testing a particular spring design may vary based on such factors as the "U"-bolt attachment geometry, axle diameter, and static loaded radius (SLR) of the particular vehicle in which the spring is to be incorporated.

Figure 6:
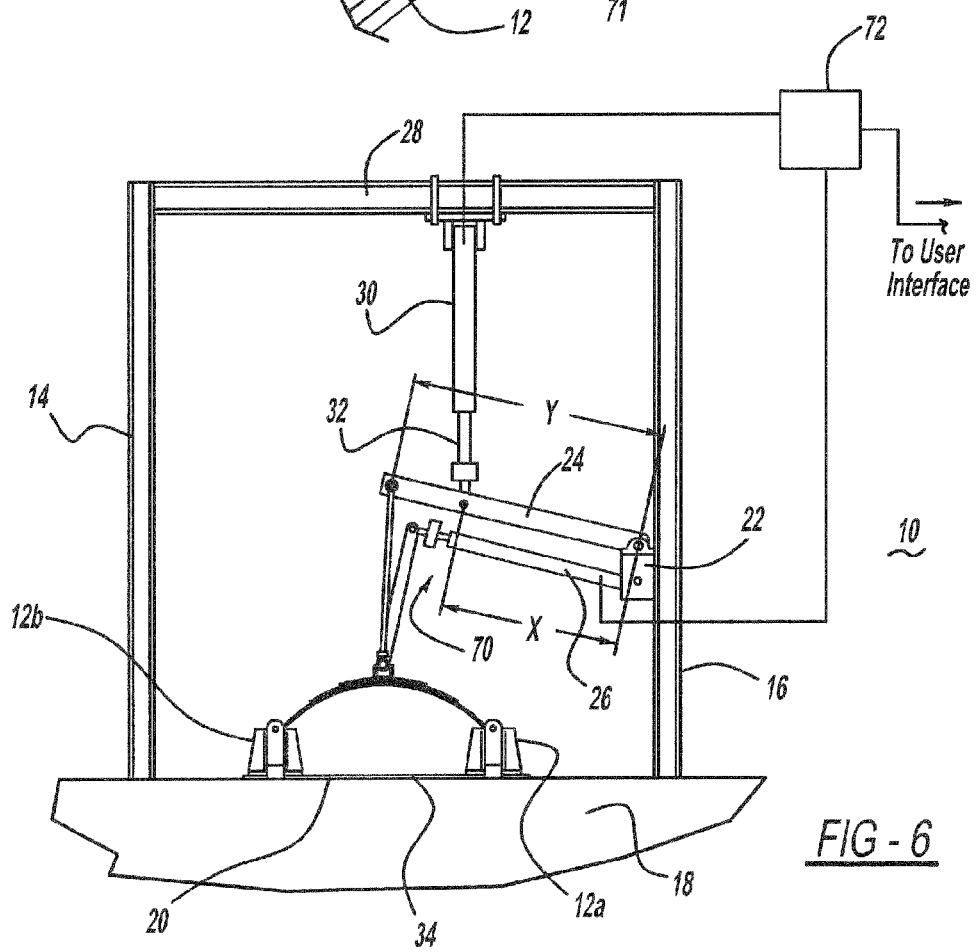
FIG. 6 is a schematic view of the testing apparatus embodiment shown in FIG. 1, showing a control system incorporated into the testing apparatus.

Referring to FIGS. 3 and 6, the piston shaft 32 through which force is transmitted from cylinder 30 to vertical force arm 24 is connected to the vertical force arm at a distance "X" from the centerline of shaft 60. Also, links 48 and 50 are rotatably connected to vertical force arm 24 at a distance "Y" from the centerline of shaft 60. The ratio "Y/X" may be specified so that a given vertical travel of cylinder piston shaft 32 produces a corresponding desired vertical displacement of axle tube fixture 52. That is, the locations of the connection points of cylinder piston shaft 32 to vertical force arm 24

(represented by distance "X") and the locations of the connection points of links 48 and 50 to the vertical force arm 24 (represented by distance "Y") can be specified so that sliding of the piston shaft 32 a predetermined distance produces a corresponding vertical displacement of axle tube fixture 52. In a particular embodiment, the ratio "Y/X" is approximately ⅔, and a piston shaft travel of 1 inch produces a vertical displacement of axle tube fixture 52 of approximately 1.5 inches. This vertical displacement of axle tube fixture 52 corresponds to a vertical displacement of the portion of spring 12 attached to the axle tube fixture 52, thereby defining the spring deflection for test purposes. It will be seen that the distances of the link and piston shaft connection points from the centerline of shaft 60 may be varied to provide any of a wide range of piston shaft stroke/axle tube fixture displacement ratios, according the requirements of a particular test regime.

Referring again to FIGS. 2, 3, and 5, a torque actuator mechanism 70 is provided for applying a torque to the axle tube fixture 52 about a centerline "M" of the axle tube fixture. The torque actuator mechanism 70 is coupled to the axle tube fixture for applying a force to the fixture to urge rotation of the fixture about axis "M". The spring member 12 is attached to the axle tube fixture 52 in the same manner as the spring would be attached to an actual vehicle axle. Thus, the torque applied to the axle tube fixture 52 is transferred to the spring member 12 to simulate the torque acting on the spring during certain predefined vehicle operational modes.

Torque actuator mechanism 70 includes an actuator (in the embodiment shown, a hydraulic cylinder 26) for supplying a force to other elements of the mechanism, and a torque input arm 82 rotatably connected to the cylinder 26 and rigidly coupled to axle tube fixture 52 for transmitting an actuation force from the cylinder 26 to the axle tube fixture.

Cylinder 26 is rotatably connected to bracket 22 via a shaft 86 extending between a pair of pillow block bearings 88, 90. Alternatively, other suitable bearing mechanisms may be used to rotatably couple the cylinder 26 to the bracket. In addition, it is seen from FIG. 3 that a centerline of shaft 86 coupling cylinder 26 to bracket 22 is aligned in a vertical plane with the centerline of shaft 60 coupling vertical force arm 24 to bracket 22. In the embodiment shown in FIGS. 1-5, cylinder 26 is mounted below vertical force arm 24 and extends substantially parallel with the vertical force arm.

A load cell 84 (for example, a strain gauge load cell) may be attached to a piston rod of the cylinder 26 to enable measurement of the force profile applied by the cylinder 26 to the spring 12 in a known manner.

In the embodiment shown in FIG. 2, torque input arm 82 is formed from a pair of parallel arm members separated by a plurality of spacers and secured together (using bolts or welds, for example) to form a single, movable piece. Alternatively, the torque input arm 82 may be formed from a single member. As seen in FIG. 2, a first end 82a of torque input arm 82 is rotatably connected to a piston shaft of cylinder 26. A second end 82b of torque input arm 82 is welded or otherwise rigidly connected to axle tube fixture 52.

In a particular embodiment, the length of the torque input arm 82 between the centerline "M" (see FIG. 5) of the axle tube fixture 52 (through which shaft 68 passes) and the centerline of a shaft 74 rotatably coupling torque input arm 82 to cylinder 26 is greater than the static loaded radius (SLR) of an actual vehicle on which the test spring is to be mounted.

In an alternative embodiment, the second end 82b of torque input arm 82 is detachably coupled to axle tube fixture 52 to enable changeover to alternative axle tube fixture designs, based on such factors as the "U"-bolt attachment geometry, axle diameter, and static loaded radius (SLR) of the particular vehicle. This also enables a vertical load (i.e., a force extending along a substantially vertical plane) to be applied to the axle tube fixture, without the simultaneous application of a torsional load.

Referring to FIG. 6, both vertical force actuator mechanism 46 and torque actuator mechanism 70 are operatively coupled to a computer-controlled electronic control system, generally designated 72. Control system 72 includes a microprocessor based electronic controller and a suitable user-interface by which a user can input or create one or more force profiles for either of (or both of) mechanisms 46 and 70. These force profiles can then be implemented by the test apparatus to test the response of the spring design to the generated forces. A user can select to separately operate either of vertical force actuator mechanism 46 and torque actuator mechanism 70, or the mechanisms may be operated simultaneously to generate and transmit a desired combined loading to the spring member.

It should be understood that the elements of torque actuator mechanism 70 are spaced apart or physically isolated from the elements of vertical force actuator mechanism 46 so as to prevent interference between the mechanisms during operation, due to contact between elements of the mechanisms. Thus, links 48 and 50 for transmission of the vertical testing force component are spaced apart from the axle tube fixture 52, which is directly connected to torque input arm 82 for producing a torsional force on the spring. Therefore, each of mechanisms 46 and 70 is capable of applying a separate force component to the spring 12 via axle tube fixture 52. A torsional load component is applied by torque actuator mechanism 70 to the spring via axle tube fixture 52, to which the spring is attached by "U"-bolts via the axle tube fixture 52. Also, a vertical load component is applied by vertical force actuator mechanism 46 to shaft 68, which is rotatably coupled to axle tube fixture 52. Stated another way, the vertical force actuator mechanism indirectly produces a motion of the axle tube fixture along a vertical plane, by moving shaft 68 which is rotatably mounted within the axle tube fixture. The torque actuator mechanism directly applies a load to axle tube fixture 52 which is manifested as a torsional load on spring 12.

By simultaneous operation of both the torque actuator mechanism 70 and the vertical force actuator mechanism 46, the effects of simultaneous torsional and vertical loading on a given spring design may be studied. Testing modes which simultaneously apply torsional and vertical loading to the spring more accurately simulate the forces operating on a spring mounted in a vehicle. This enables a more accurate understanding of spring failure modes.

Furthermore, because operation of the actuator mechanisms 46 and 70 is controlled by a micro-processor based electronic controller, any of a wide variety of user-generated force profiles can be implemented by the test apparatus, to test the response of the spring design to a wide variety of operating conditions.

It will be understood that the foregoing description of an embodiment of the present invention is for illustrative purposes only. As such, the various structural and operational features herein disclosed are susceptible to a number of modifications commensurate with the abilities of one of ordinary skill in the art, none of which departs from the scope of the present invention as defined in the appended claims.

What is claimed is:

1. An apparatus structured for testing a spring member, the apparatus comprising:
  a fixture securable to a portion of a spring member structured as a component of a vehicle suspension system;

a first mechanism operatively coupled to the fixture for applying a translational loading to the portion of the spring member via the fixture; and
a second mechanism operatively coupled to the fixture for applying a torsional loading to the portion of the spring member via the fixture.

2. The apparatus of claim 1 wherein the first mechanism is detachably coupled to the fixture.

3. The apparatus of claim 1 wherein the second mechanism is detachably coupled to the fixture.

4. The apparatus of claim 1 wherein the spring member for which the apparatus is structured for testing is a leaf spring.

5. An apparatus for testing a spring member, the apparatus comprising:
a fixture securable to a portion of the spring member;
a first mechanism operatively coupled to the fixture for applying a translational loading to the portion of the spring member via the fixture; and
a second mechanism operatively coupled to the fixture for applying a torsional loading to the portion of the spring member via the fixture,
wherein the first mechanism includes a plurality of first elements, the second mechanism includes a plurality of second elements, and wherein each first element of the plurality of first elements is spaced apart from each second element of the plurality of second elements for preventing interference between the first and second mechanisms during operation of the first and second mechanisms.

6. An apparatus for testing a spring member, the apparatus comprising:
a fixture securable to a portion of the spring member;
a first mechanism operatively coupled to the fixture for applying a translational loading to the portion of the spring member via the fixture;
a second mechanism operatively coupled to the fixture for applying a torsional loading to the portion of the spring member via the fixture,
wherein the first mechanism includes:
an actuator mounted on a frame, the actuator including a shaft;
a force arm connected to the actuator shaft and rotatably coupled to the frame; and
at least one link rotatably coupled to the force arm and to the fixture for transmitting a force from the actuator to the fixture.

7. The apparatus of claim 6 wherein the actuator is mounted on the frame so as to enable repositioning and securement of the actuator to the frame at any location along a predetermined portion of the frame.

8. The apparatus of claim 6 wherein the force arm is rotatably coupled to the frame so as to enable repositioning and securement of a portion of the force arm to the frame at any location along a predetermined portion of the frame.

9. In an apparatus in accordance with claim 6, a method for loading a spring member secured thereto so as to produce a desired predetermined displacement of the fixture responsive to a given displacement of the actuator shaft, the method comprising the steps of:
connecting the force arm to the at least one link at a first distance from a connection between the force arm and the frame and connecting the force arm to the actuator at a second distance from a connection between the force arm and the frame such that a ratio of the first distance to the second distance equals a ratio of the desired predetermined displacement to the given displacement; and
displacing the actuator shaft an amount equal to the given displacement.

10. The method of claim 9 wherein the ratio of the first distance to the second distance is equal to approximately 3/2.

11. An apparatus for testing a spring member, the apparatus comprising:
a fixture securable to a portion of the spring member;
a first mechanism operatively coupled to the fixture for applying a translational loading to the portion of the spring member via the fixture;
a second mechanism operatively coupled to the fixture for applying a torsional loading to the portion of the spring member via the fixture,
wherein the second mechanism includes:
an actuator rotatably coupled to a frame; and
a torque arm rotatably connected to the actuator and rigidly coupled to the fixture for transmitting a force from the actuator to the fixture.

12. The apparatus of claim 11 wherein the actuator is rotatably coupled to the frame so as to enable repositioning and securement of the actuator to the frame at any location along a predetermined portion of the frame.

13. An apparatus for testing a spring member, the apparatus comprising:
a fixture securable to a portion of the spring member;
a first mechanism operatively coupled to the fixture for applying a translational loading to the portion of the spring member via the fixture; and
a second mechanism operatively coupled to the fixture for applying a torsional loading to the portion of the spring member via the fixture,
the apparatus further comprising a mounting base for securing the spring member thereto, the mounting base being positioned with respect to the fixture so as to enable securement of the fixture to the portion of the spring member when the spring member is secured in the mounting base.

14. The apparatus of claim 13 wherein the mounting base includes a base portion, a first mounting block securable to the base portion, and a second mounting block securable to the base portion opposite the first mounting block.

15. The apparatus of claim 14 wherein at least one of the first mounting block and the second mounting block is adjustably positionable with respect to the other of the first mounting block and the second mounting block.

16. The apparatus of claim 14 wherein at least one of the first mounting block and the second mounting block is configured so as to enable adjustment of a height above the base portion of a portion of the spring member connected to the at least one of the first mounting block and the second mounting block.

17. The apparatus of claim 13 wherein the mounting base is adjustably positionable with respect to the fixture.

18. An apparatus structured for testing a spring member, the apparatus comprising:
a frame;
a first mechanism operatively coupled to the frame for applying a translational loading to the spring member, the first mechanism including a plurality of first elements; and
a second mechanism operatively coupled to the frame for applying a torsional loading to the spring member, the second mechanism including a plurality of second elements,
wherein each first element of the plurality of first elements is spaced apart from each second element of the plurality of second elements for preventing interference between the first and second mechanisms during operation of the first and second mechanisms.

19. An apparatus structured for testing a spring member, the apparatus comprising:
- a fixture for securing a portion of a leaf spring thereto, the leaf spring being structured as a component of a vehicle suspension;
- a first mechanism operatively coupled to the fixture for applying a force to the fixture to urge movement of the fixture along a plane; and
- a second mechanism operatively coupled to the fixture for applying a force to the fixture to urge rotation of the fixture about an axis.

20. The apparatus of claim 19 wherein the spring member for which the apparatus is structured for testing is a configured as a component of a vehicle suspension system.

* * * * *